United States Patent [19]
Khandke

[11] Patent Number: 6,150,151
[45] Date of Patent: Nov. 21, 2000

[54] AFFINITY CHROMATOGRAPHIC MATRIX CONTAINING NON-COVALENTLY BOUND LIGAND FOR PURIFICATION OF BIOLOGICAL MATERIAL

[75] Inventor: Kiran Manohar Khandke, Nanuet, N.Y.

[73] Assignee: American Cyanamid Company, Madison, N.J.

[21] Appl. No.: 08/292,162

[22] Filed: Aug. 17, 1994

Related U.S. Application Data

[63] Continuation of application No. 08/031,158, Mar. 12, 1993, abandoned.

[51] Int. Cl.[7] .................. C12N 9/24; G01N 33/544; C07K 1/22; C07K 17/10
[52] U.S. Cl. .................. 435/200; 435/178; 435/180; 435/181; 435/196; 435/815; 436/529; 436/824; 530/413; 530/813; 536/21
[58] Field of Search .................. 435/178, 180, 435/181, 196, 200, 815; 436/529, 824; 530/413, 813; 536/21

[56] References Cited

U.S. PATENT DOCUMENTS

| | | | |
|---|---|---|---|
| 3,843,443 | 10/1974 | Fishman | 195/63 |
| 4,693,985 | 9/1987 | Degen et al. | 435/180 X |
| 4,954,444 | 9/1990 | Eveleigh et al. | 435/181 |
| 4,981,961 | 1/1991 | Ngo | 435/181 X |
| 5,198,355 | 3/1993 | Kikuchi et al. | 435/177 X |

OTHER PUBLICATIONS

Messing, Ralph, A., Methods in Enzymology, Vol. XLIV, 1976 (pp. 148–167).

*Primary Examiner*—David M. Naff
*Attorney, Agent, or Firm*—Rebecca R. Barrett

[57] ABSTRACT

An affinity chromatographic matrix for purification of a biological material is provided having an ionically charged polymeric ligand such as glycoaminoglycan non-covalently bound directly by an ionic bond to an oppositely ionically charged group on a chromatographic matrix. Having the ligand non-covalently bound to the matrix by an ionic bond, allows the ligand to be easily washed off the matrix and replaced for subsequent purifications without having to replace the matrix. A biological material in a crude mixture is purified by non-covalently binding the material to the bound ligand and dissociating the material from the ligand. Matrices that may be used include crosslinked agarose, crosslinked dextran, crosslinked cellulose, crosslinked dextran and bisacrylamide, or matrices based on silica or plastic polymers. The charged group may be a quaternary amine or diethylaminoethyl group. Chondroitinase is purified from a crude mixture containing contaminating proteins by contacting the crude mixture with an anion exchange resin containing chondroitin sulfate non-covalently bound by an ionic bond. Chondroitinase non-covalently binds to the bound chondroitin sulfate and contaminating proteins pass through the matrix. Chondroitinase is then dissociated from the matrix.

9 Claims, 1 Drawing Sheet

AFFINITY CHROMATOGRAPHIC MATRIX CONTAINING NON-COVALENTLY BOUND LIGAND FOR PURIFICATION OF BIOLOGICAL MATERIAL

This is a continuation of application Ser. No. 08/031,158 filed on Mar. 12, 1993, now abandoned.

FIELD OF THE INVENTION

The present invention relates to methods for purifying biological molecules employing affinity chromatography. In particular, the present invention is directed to an affinity chromatography technique employing a highly charged polymeric ligand non-covalently bound to a charged support.

BACKGROUND OF THE INVENTION

Affinity chromatography is a separation technique which is based on the specific binding properties of biological molecules. Briefly, the methodology of affinity chromatography involves the attachment of a specific ligand to an insoluble support or matrix to form a conjugate which is then contacted with a "feed" containing the substance to be purified either in a column or batch configuration. Contact of the feed with the conjugate results in the substance that reacts specifically with the ligand becoming attached to the conjugate with all the remaining components of the feed passing through the column in the void volume. The adsorbed substance is then eluted from the column by imposing conditions which dissociate it from the conjugated ligand. Preferably, the column can then be recycled and the affinity adsorbent reused for additional purifications.

Generally speaking, an affinity chromatography system has several components; a support for attaching the ligand, which is generally made from a polysaccharide but may also be made from other materials such as polyacrylamide gel, silica, other polymers or glass; optionally a spacer or "arm" between the ligand or support used to contribute to the binding of macromolecules such as proteins to affinity columns; and the ligand which is specifically designed based on its capability to bind to the substance to be purified. The ligand may be an enzyme, co-enzyme, the substrate or inhibitor of an enzyme, an antibody, an antigen, and the like.

With respect to the support components of the affinity chromatography system, a number of materials suited for use with multiple ligands are commercially available. Most commonly, the ligand is covalently bound to the support and for this purpose so called "activated" supports which are pre-configured for covalent linkage with ligands are commercially available.

In order for the affinity chromatography system to be recycled it is desirable that the support and ligand be resistant to breakdown during the purification process. However, severe shortcomings are encountered as a result of the instability of the covalent chemical linkages between the support and the ligand. Polysaccharide supports such as agarose using covalently coupled ligands are susceptible to microbial attack and suffer from instability with respect to mechanical destruction and "ligand leakage" on prolonged washing. When the ligand is a polysaccharide (for example chondroitin sulfate) these same problems of microbial attack, mechanical destruction and "ligand leakage" become important considerations. When the affinity chromatography system uses an enzyme substrate as a ligand which is covalently bound to the support, the ligand is highly susceptible to breakdown by the enzyme during the purification process destroying the integrity of the support-ligand attachment which requires replacement of the affinity chromatography system. Repeated cycling of the covalently coupled system invariably results in a lowering of binding capacity and in extreme cases, binding capacity can be totally lost due to cleavage of the polysaccharide ligand by the enzyme or by microbial attack. Due to the high cost of the so called "activated" matrix supports which utilize covalent coupling, replacement of the systems becomes an expensive drawback to the affinity chromatography purification technique.

There is thus a need for an affinity chromatography system which avoids the shortcomings and expense associated with conventional covalently coupled systems and allows replacement of the ligand to be accomplished simply and without the need to replace the entire matrix support system.

SUMMARY OF THE INVENTION

Figure 1:
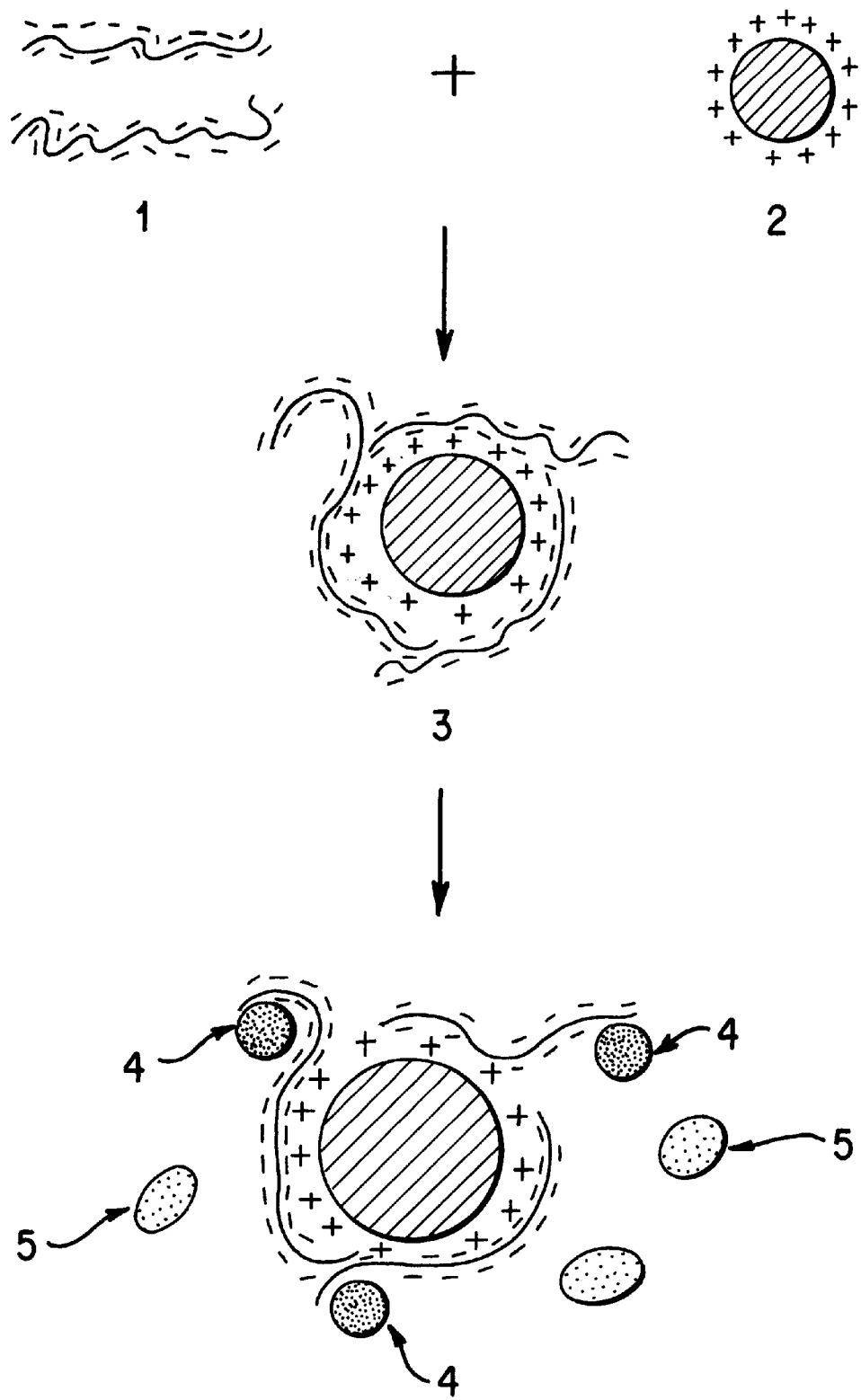
FIG. 1 is a diagram illustrating the preparation and use of an affinity chromatography system of this present invention.

The present invention relates to an affinity chromatography system for purification of biological materials comprising a charged polymer ligand non-covalently bound to a charged support. The ligand and support are bound by ionic interactions which arise from oppositely charged materials. Utilization of the non-covalently bound ligand allows the ligand to be easily washed off the support and replaced for subsequent purifications without the need to replace expensive supports which use covalently bound ligands.

Preferably, the support used is a charged polymeric matrix such as that used in ion-exchange chromatography. The matrix could be any of the commercially available gels like Sepharose (crosslinked agarose), Sephacryl (crosslinked dextran and bis acrylamide), Sephadex (crosslinked dextran), Sephacel (crosslinked cellulose), as well as matrices based on silica or plastic polymers. The charged group on these matrices could be Q (quaternary amine), DEAE (diethylaminoethyl), if the ligand to be non-covalently coupled is a negatively charged polymer; or CM(carboxymethyl) or S(sulfate), if the ligand is positively charged. Other less commonly used charged groups would also work as long as the charge is sufficient to retain the polymer throughout the affinity chromatography process.

The ligand suitable for use in the present invention is any ligand which is naturally a highly charged polymer in solution which will form non-covalent ionic bonds with the support matrix. Of course, selection of the ligand will be specific to the material which it is designed to purify. In general, the affinity chromatography system of the present invention may be used to purify any enzyme which has a charged polymer as a substrate. As stated, any highly charged polymeric ligand will be useable in the present invention including, for example, chondroitin sulfate, deacetylated chondroitin sulfate or other glycoaminoglycans such as heparin sulfate, dermatan sulfate, hyaluronic acid and the like. It is necessary that the ligand carry enough charge per molecule to bind to the support yet leave enough exposed surface for the ligand to interact with the material to which it binds in the feed. For this reason, long chain polymers with multiple charged residues such as charged polysaccharides or glycoaminoglycans are best suited for preparing the affinity gel of the present invention. Preferably, the polymer has a charge to mass ratio of about 1:200 as is seen for chondroitin sulfate. Another property of a potential ligand would be the presence of a single charged species being repeated along the polymer chain at regular intervals (negative charge in chondroitin sulfate for example), which would result in tight binding (exponential effect).

FIG. 1 illustrates the preparation and use of an affinity chromatography system of the present invention. Excess charged polymeric ligand 1 is incubated with the charged affinity gel support 2 and dialyzed against water. The ligand 1 and support 2 are then non-covalently bound forming the affinity gel 3 and leaving portions of the polymer exposed for interaction with the enzyme, or other material to be purified. The crude mixture to be purified is then contacted with the affinity gel 3 in a column or batch configuration and the molecules of the substance to be purified 4 bind to the ligand and are separated from molecules of the crude mixture 5 as shown in FIG. 1. The purified substance is then eluted from the gel by imposing conditions which dissociate it from the gel.

A modified version of this method has been effective in a column format, where the enzyme of interest is simply retarded, eluting several bed volumes later than the contaminating proteins, which elute at the first bed volume, resulting in a pure protein in a single step. This phenomenon could be either due to weak/low affinity binding of the enzyme to the ligand or strong high affinity binding followed by enzymatic cleavage of the ligand, resulting in the eventual release of the enzyme.

The specific advantage of the present invention over the conventional covalently coupled affinity gels, is the ability to replace the ligand after several cycles of use by a simple process of regenerating the gel(with an acid, alkali cycle) and re-incubating the gel with ligand, eliminating the need to replace the entire gel matrix as in conventional covalently coupled gels, which is an expensive procedure. Other advantages include the simplicity with which the gel can be prepared as compared to covalently coupled gels and the reduced cost of the support matrix affinity gel, as the expensive so-called "activated" gels are not necessary.

DETAILED DESCRIPTION

Preparation of the Affinity Gel

A) The Support—the characteristics of a suitable support for use with the present invention may be summarized as follows:

1) The support must be capable of forming non-covalent bonds with the ligand. Charged ion-exchange gels are suitable for this purpose;
2) The support should be homogeneous in form to allow good flow properties in columns and allow a large effective surface area for attachment of the ligand and its interaction with the desired component of the feed;
3) The support should have good mechanical, physical and chemical stability;
4) The support should be insoluble in the operating medium or easily separated by filtration or otherwise from the medium.

Among the charged support materials that are suitable for use in the present invention are simple or cross-linked polymers of cellulose, agarose, dextran, acrylamide, or other natural or synthetic material having charged moieties such as Q-(quaternary amine) or DEAE (diethylaminoethyl) and any positively charged support when the ligand is negatively charged, and CM (carboxymethyl), S (sulfate) and any negatively charged support for positively charged ligands.

B. The Ligand—the characteristics of a suitable ligand for the present invention are as follows:

1) As stated, it must be a highly charged polymeric ligand capable of forming non-covalent ionic bonds with the support gel.
2) It must have the necessary specificity and strength of binding to the component of the feed which it is desired to be purified. Since the ligand will necessarily carry substantial charge, it will be necessary to be able to minimize interference effects from non-specific ion-exchange type of adsorption of undesired materials in the feed onto the ligand. In such cases, elution procedures must be employed which distinguish between material bound ionically to the ligand and material bound through specific affinity to the ligand.
3) The binding of the ligand to the desired component should be reversible.

C) Coupling—the coupling of the ligand and support is generally done by incubating excess ligand with the support and dialyzing the mixture against water. The activated support can generally be stored under appropriate conditions depending on the nature of the ligand and support. When Q-SEPHAROSE (Pharmacia LKB Biotechnology Inc., Piscataway, N.J.) and chondroitin sulfate was used, the gel was stored in 20% ethanol at 4° C. with excess substrate. This preparation is stable for at least six months.

Chromatography

A) Binding—The crude mixture to be purified is loaded at appropriate conditions to promote binding to the immobilized ligand with minimal cleavage. Under appropriate conditions, the desired component binds to the ligand while other components of the crude mixture are washed off in the flow-through, thus achieving the desired separation.

B) Elution—Elution is accomplished according to the separation desired.

The following example is provided by way of illustration and should not be interpreted as limiting the invention, many variations of which are possible without departing from the spirit or scope thereof:

EXAMPLE 1

The affinity chromatography method of the present invention is used to purify chondroitinase, an enzyme which acts on chondroitin sulfate, the molecule which mediates the attachment between the retina and vitreous body. The enzyme has potential use in ocular surgery as a means for rapid and specific non-surgical disruption of this attachment, facilitating removal of the vitreous body.

Chondroitin sulfate is used as the ligand and Q-sepharose as the support. DEAE is also found to be effective in binding chondroitin sulfate, but Q-sepharose is preferred as it binds more chondroitin sulfate per ml. of gel.

Coupling is done by incubating excess chondroitin sulfate with Q-SEPHAROSE (Pharmacia LKB Biotechnology Inc., Piscataway, N.J.) (100 mg/ml gel), and dialyzing the mixture against water. The gel is saturated with about 24 mg/ml gel. The gel may then be stored in 20% ethanol at 4° C. with the excess substrate. This preparation is stable for at least six months under these conditions.

To purify the chondroitinase from the crude mixture, the crude mixture containing chondroitinase is loaded at pH 7–8. The whole operation is done at 4° C. to promote binding to the coupled substrate with minimal cleavage. Chondroitinase binds under these conditions while most contaminating proteins are washed off in the flow-through, thus achieving the desired separation.

Elution can be done according to the separation desired. In most cases, a gradient of chondroitin sulfate is used, which competes with the chondroitin sulfate on the gel for the enzyme, resulting in elution. An increasing gradient of chondroitin sulfate may also be used along with a simultaneous decreasing gradient of buffer, with a view of keeping the conductivity relatively constant during elution and hence increasing the specificity of elution due to affinity versus nonspecific elution due to salt/buffer.

As a variation, this affinity matrix can be used to separate two closely related forms of the active enzyme, not separable by other techniques like ion-exchange or gel permeation chromatography (GPC): e.g. Purification of chondroitinase from a recombinant derived crude preparation. Total activity loaded 21,250 units in 16 ml. Bed volume of Q-Sepharose-Chondroitin sulfate column, 25 ml specific activity of chondroitinase at start 174 unit or mg protein. The chondroitinase after purification is 99% pure SDS-PAGE, N-terminal sequencing gives a single sequence, corresponding to the uncleaved 110 kDa chondroitinase sequence. The recovery is 96% of the load. The specific activity of the purified protein is 556 units/mg.

I claim:

1. An affinity chromatographic matrix comprising a charged polymeric ligand non-covalently bound to an oppositely charged chromatographic matrix, wherein the charged polymeric ligand is directly bound by an ionic bond to an oppositely charged group on the chromatographic matrix, and said ligand is capable of non-covalently binding a biomacromolecule to purify the biomacromolecule.

2. An affinity chromatographic matrix of claim 1 wherein the ligand is a glycoaminoglycan.

3. An affinity chromatographic matrix of claim 1 wherein the ligand is a polysaccharide.

4. An affinity chromatographic matrix of claim 1 in which the charged chromatographic matrix is a gel having a positively charged group selected from the group consisting of a quaternary amine and diethylaminoethyl.

5. An affinity chromatographic matrix of claim 1 in which the ligand is chondroitin sulfate, deacetylated chondroitin sulfate, heparin sulfate, dermatan sulfate or hyaluronic acid.

6. In a process for purifying a biomacromolecule by affinity chromatography with a chromatographic matrix, the improvement which comprises employing as the chromatographic matrix, an ionically charged chromatographic matrix to which an oppositely ionically charged ligand is non-covalently directly attached by an ionic bond, said ligand being selected from the groups consisting of chondroitin sulfate, deacetylated chondroitin sulfate, heparin sulfate, dermatan sulfate and hyaluronic acid, and said attached ligand being capable of non-covalently binding said biomacromolecule.

7. A process for purification of chondroitinase which comprises contacting crude chondroitinase containing material with an affinity chromatographic matrix comprised of an anion exchange resin to which chondroitin sulfate is non-covalently directly bound by an ionic bond, for a time sufficient to permit binding of chondroitinase non-covalently to said chondroitin sulfate bound to said affinity chromatographic matrix while washing contaminating proteins through said matrix, followed by dissociation of said chondroitinase from said matrix.

8. The process of claim 7 in which said chondroitinase is loaded on said affinity chromatographic matrix at a pH of 7–8.

9. The process of claim 7 in which said anion exchange resin is Q-Sepharose.

* * * * *